US009506868B2

(12) United States Patent
Boufendi et al.

(10) Patent No.: US 9,506,868 B2
(45) Date of Patent: Nov. 29, 2016

(54) METHOD AND SYSTEM FOR ANALYZING PARTICLES IN COLD PLASMA (71) Applicants: CENTRE NATIONAL DE LA RECHERCHE SCIENTIFIQUE, Paris (FR); UNIVERSITE D'ORLEANS, Orleans (FR); COMPAGNIE INDUSTRIELLE DES LASERS CILAS, Orleans (FR); INSTITUT NATIONAL DE L'ENVIRONNEMENT INDUSTRIEL ET DES RISQUES, Verneuil-en-halatte (FR)

(72) Inventors: Laïfa Boufendi, Saint Denis en Val (FR); Laurent Meyer, L'Isle Adam (FR); Christophe Dutouquet, Senlis (FR); Emeric Frejafon, Villiers Sous Saint Leu (FR); Gaétan Wattieaux, Vigoulet-Auzil (FR)

(73) Assignees: Centre National De La Recherche Scientifique, Paris (FR); Universite D'Orleans, Orleans (FR)

( * ) Notice: Subject to any disclaimer, the term of this patent is extended or adjusted under 35 U.S.C. 154(b) by 0 days.

(21) Appl. No.: 14/431,727

(22) PCT Filed: Sep. 27, 2013

(86) PCT No.: PCT/FR2013/052300
§ 371 (c)(1),
(2) Date: Mar. 26, 2015

(87) PCT Pub. No.: WO2014/049291
PCT Pub. Date: Apr. 3, 2014

(65) Prior Publication Data
US 2015/0241357 A1 Aug. 27, 2015

(30) Foreign Application Priority Data

Sep. 27, 2012 (FR) ..................................... 12 59101

(51) Int. Cl.
G01J 3/30 (2006.01)
G01N 21/71 (2006.01)
H05H 1/00 (2006.01)

(52) U.S. Cl.
CPC .......... *G01N 21/718* (2013.01); *H05H 1/0037* (2013.01)

(58) Field of Classification Search
CPC ............... G01N 21/718; G01N 21/67; G01N 21/3103; G01N 21/62; G01N 21/6402; G01N 21/73; G01N 21/68; G01N 21/645; H05H 1/0037; H05H 1/30
USPC .................................................. 356/300–445
See application file for complete search history.

(56) References Cited

U.S. PATENT DOCUMENTS 4,199,685 A * 4/1980 Hora ....................... B01D 59/34
250/423 P
2005/0147765 A1* 7/2005 Dose ....................... C23C 16/27
427/460
2008/0239312 A1* 10/2008 Hori ........................ G01J 3/443
356/326

FOREIGN PATENT DOCUMENTS

FR 2937419 A1 4/2010
FR 2938066 A1 5/2010

OTHER PUBLICATIONS

Eom GS et al; Size Determination of Nanoparticles in Low-Pressure with Laser-Induced Incandescene Technique, Applied Physics Letters, American Institute of Physics, vol. 83, No. 6, Aug. 11, 2003; pp. 1261-1263.
International Search Report from International Application No. PCT/FR2013/052300 mailed Nov. 28, 2013; 4 pages.

* cited by examiner

*Primary Examiner* — Abdullahi Nur
(74) *Attorney, Agent, or Firm* — Lee & Hayes, PLLC (57) ABSTRACT The invention relates to a method of analyzing particles, in particular particles of diameter less than 1 μm, the method comprising the following steps:
 firing laser shots into a cold plasma (45) at low pressure;
 using an optical spectrometer device (60) to acquire emission spectra of the light emitted by the plasma as a result of the laser shots, in such a manner that for each acquired spectrum, an acquisition period begins no later than 100 ns after firing the laser shot; and
 analyzing the particles present in the plasma on the basis of the emission spectra.
A system for detecting and/or analyzing particles by performing the method.

13 Claims, 5 Drawing Sheets

METHOD AND SYSTEM FOR ANALYZING PARTICLES IN COLD PLASMA

CROSS-REFERENCE TO RELATED APPLICATIONS

This Application is the National Stage of International Application No. PCT/FR2013/052300, filed Sep. 27, 2013, which claims priority to French Patent Application No. 1259101, filed Sep. 27, 2012, the entire disclosures of which are incorporated herein by reference.

The invention relates to a method of analyzing particles of small diameter, i.e. of diameter less than 1 micrometer (μm). By way of example, but not exclusively, these particles may be nanoparticles, e.g. formed by laser pyrolysis. The particles may be liquid or solid, inorganic or organic. By way of example, they may be microorganisms, such as bacteria. The size of the particles may also reach several micrometers.

The invention relates in particular to analyzing particles contained in a cold plasma, which is maintained at very low pressure, i.e. at a pressure of less than 10 millibar (mbar), or indeed less than 1 mbar.

Such a pressure is referred to below as a "low" pressure.

The term "cold plasma" is used herein to designate a plasma that is not in thermodynamic equilibrium. In the cold plasmas under consideration, the energy of electrons is generally less than 10 electron volts (eV), and in practice may for example be close to 3 eV to 5 eV. The energy of neutral species and of ions (heavy species) generally remains less than one-tenth of an electron volt.

As knowledge about plasmas progresses, matter is being taken to the cold plasma state in an increasing number of circumstances, and in particular in industrial processes.

It is possible that particles are formed in the plasma during this stage, or indeed that particles are present in the plasma for other reasons.

It can be necessary or useful to analyze the particles or the composition of particles present in a plasma (i.e. in this document, determining the composition means determining the stoichiometry of the elements making up the particles under analysis, or in other words determining the relative proportions of these elements within the particles).

In known manner, in order to evaluate the composition of particles present in a plasma, the particles are collected in a container, and transported to a laboratory, where they are analyzed by known analysis means, such as optical spectrometry.

That method presents the drawback of results becoming known a relatively long time after the particles have been detected and collected from within the plasma. When the results of such analysis are useful for controlling continuous fabrication, it can happen that production is non-compliant throughout all of the time required for obtaining analysis results. Thus, the shorter the time required for analysis, the smaller the quantity of non-compliant product that is produced.

Determining the size of particles present in a low-pressure plasma is also known, e.g. from the document "Size determination of nanoparticles in low-pressure plasma with laser-induced incandescence technique", by G. S. Eom et al., Applied Physics Letters, AIP American Institute of Physics, Melville, N.Y., USA, Vol. 83, No. 6, Aug. 11, 2003 (2003 Aug. 11), pp. 1261-1263, XP012035779, ISSN: 0003-6951, DOI: 10.1063/1.1599965.

According to that document, it is possible to determine the size of particles present in a low-pressure plasma as follows:
laser shots are fired into the low-pressure plasma;
particles heated by the laser shots then emit radiation; and
some of that radiation is captured by a photomultiplier tube and transmitted to an acquisition device.

The signal obtained can then be analyzed. The size of the particles is calculated by making use of the relationship between particle size, temperature variation, and the thermal properties of the material constituting the particle.

Nevertheless, that method is capable only of obtaining the size of the analyzed particles, and not their composition. On the contrary, it appears to be inapplicable when it comes to analyzing the composition of particles: it requires a priori knowledge about the composition of the material in order to be able to select an appropriate wavelength for the laser, since otherwise the signal returned by the particles might not be sufficient.

It is also known to measure the composition of particles diluted in a gas stream by the laser-induced breakdown spectroscopy (LIBS) method. That method is disclosed in particular in patent application FR 2 937 419, in the name of one of the joint Applicants.

That analysis method is known only for analyzing particles diluted in a gas that, a priori, has a pressure close to that of atmospheric pressure.

Under such pressure conditions, laser shots serve to create microplasmas locally. Those microplasmas are created within the gas itself, and not in the particles, which are at a very low concentration. After being "ignited", those microplasmas are the subject of very strong expansion; their volume is multiplied by a factor that is of the order of one thousand. During that expansion, they absorb particles; the particles absorbed in that way become dissociated (or at least some of them do). Particle dissociation in the microplasmas therefore does not occur directly under the effect of laser shots, but only after the particles have been absorbed by the microplasmas.

In practice, the laser-induced microplasmas created when performing the method of Document F 2 937 419 encompass several hundreds of particles, thereby leading to considerable radiation from those particles.

That method therefore requires a gas to be present, with the particles being in the gas, and with the gas being capable of being taken to the plasma state by laser shots.

Unfortunately, in a low-pressure plasma, gas pressure is extremely low. Consequently, laser shots do not enable microplasmas to be generated in the gas itself.

Consequently, in low-pressure plasmas, firing laser shots does not a priori make it possible to form microplasmas in which particles are dissociated as a result of the microplasmas expanding.

Finally, the method proposed in Document FR 2 937 419 is performed in a neutral gas stream in which high concentrations of particles are conveyed.

The method proposed in Document FR 2 937 419 would appear to be unsuitable for use in analyzing particles that are contained at low concentrations in a low pressure cold plasma. It does not provide for any way of trapping and analyzing an individual particle.

For those various reasons, the method proposed by Document FR 2 937 419 appears to be unsuitable for use in analyzing particles contained in a low pressure cold plasma.

There therefore exists a need for a method of analyzing particles present in a low pressure cold plasma and that is capable, in particular, of providing information about the presence and the composition of particles within the plasma under examination, and of doing so more quickly than known methods.

The first object of the invention is to satisfy that need.

To do this, the invention firstly provides a method of analyzing particles, in particular particles of diameter less than 1 µm, the method comprising the following steps:

a) providing a cold plasma at a pressure less than 10 mbar, and preferably less than 1 mbar;

b) firing laser shots into the cold plasma;

c) using an optical spectrometer device to acquire emission spectra of the light emitted by the plasma as a result of the laser shots, in such a manner that for each acquired spectrum, an acquisition period begins no later than 100 nanoseconds (ns) after firing the laser shot; and d) detecting the presence of particles in the plasma on the basis of said emission spectra.

The optical spectrometer device mainly comprises a light collector connected to an optical spectrometer, itself coupled to a detector.

It is found that particles forming part of a low-pressure plasma can be analyzed by laser-induced optical spectroscopy (LIBS method).

As mentioned above, when the laser shots are fired, the gas molecules are too diffuse to enable a local microplasma to be created.

Conversely, the particles themselves can be irradiated by the laser shots (generally nanosecond shots) that are highly energetic. When a shot hits a particle, it causes the particle to be partially or completely dissociated, thereby forming a microplasma.

The light emitted by the microplasma contains the chemical signatures of all of the elements contained in the particles present in the sampling volume, i.e. of all the particles that are irradiated by the laser. Consequently, using an optical spectrometer to analyze this light makes it possible to detect the presence of particles, and/or to determine the stoichiometric composition of elements in the particles.

Because the pressure in the plasma is extremely low, the gas molecules surrounding the particles and captured in the microplasma generate practically no radiation. Consequently, the emission spectra presents an excellent signal-to-noise ratio, which is essential if the particles for analysis are present at very low concentrations only.

Thus, the method of the invention can be performed in a plasma in which the concentration of particles in the cold plasma is less than $10^8$ particles per cubic centimeter ($cm^3$), or indeed $10^6$ particles/$cm^3$, or even $10^5$ particles/$cm^3$.

The microplasmas generated by the particles struck by the laser shots are transient, with their lifetimes being estimated as being only a few hundreds of nanoseconds.

That is why, in the invention (and unlike the prior method of analyzing particles as disclosed in Document FR 2 937 419), it is important to begin acquiring emission spectra with the spectrometer device no later than 100 ns after firing the laser shot or after firing each laser shot.

This acquisition window beginning very shortly after firing the laser shot makes it possible to capture most of the radiation emitted by the microplasma. This radiation falls off quickly, and typically it becomes imperceptible after a duration of 1 microsecond (µs) to 2 µs.

The signal may begin to be recorded beginning a few tens of nanoseconds after firing the laser shot, and it may continue generally for a few microseconds. The exposure time (recording duration) is generally less than 1 µs, or possibly less than 5 µs.

The invention thus constitutes a novel method of measuring particles, and in particular nanoparticles, that can be used in any low pressure cold plasma, and in particular in a cold plasma generated by radiofrequency (RF) discharges.

This method may be used in various circumstances or various contexts.

The cold plasma provided in step a) may initially be a plasma that results from performing an industrial process.

The method may thus be used for quality control of a fabrication process in which a cold plasma is formed, whenever it is necessary to evaluate the presence and/or the composition of particles in the cold plasma.

Examples of processes in which a cold plasma is formed include certain processes for fabricating nanoparticles, or for forming thin-film coatings by physical vapor deposition (PVD), or indeed by plasma enhanced chemical vapor deposition (PECVD). The plasma may contain particles that can be useful or necessary to detect and analyze.

Nevertheless, the plasma may also be generated specifically in order to be able to perform the method of the invention. The plasma may be put into levitation; it then acts as a trap, which is used specifically for trapping particles, if any, in order to detect them and/or analyze them.

Under certain circumstances, step a) of the method of the invention (providing a cold plasma) may be performed in two stages: in a first stage a1) a cold plasma is formed, and then in a second stage a2) the particles are introduced into the plasma. The cold plasma mentioned in step b) is then the plasma containing particles as obtained at the end of stage a2).

Step a) of the method may also be a step during which particles form inside a plasma, in particular as a result of chemical reaction between gas molecules that are present.

Under such circumstances, the cold plasma mentioned in step b) is the plasma containing particles as obtained after the above-mentioned particle-forming reaction.

It can be understood that when the plasma is generated specifically for performing the method of the invention, the method may be used for quality control of any atmosphere or gaseous phase, such as for example for detecting and/or analyzing particles in gases produced by industrial processes.

The method makes it possible in particular to detect various elements such as organic particles, bundles of carbon nanotubes, bacteria, particles of titanium oxide, etc., that it may be important to detect, and in particular at low concentrations.

Advantageously, the method may be performed on site, in line, and may provide results almost in real time. It is thus particularly well adapted to any industrial process in which particles are produced.

In an implementation, the method further includes a step of estimating the concentration of particles in the plasma.

It may also include a step of calculating the concentration of particles in the (gaseous) medium in which the plasma has been formed in step a).

The concentration of particles may be calculated in particular in plasmas containing particles at low density.

The calculation may be performed as follows:

For each laser shot, it is detected that a particle has been hit by the shot when the emission spectrum contains one or more emission lines characteristic of the elements constituting the particles. The probability of particles being present is then calculated by taking the ratio of the number of particles detected to the number of laser shots.

Thereafter, an order of magnitude is estimated for the sampling volume.

The concentration of particles is then obtained by dividing the probability of a particle being present in the sampling volume of the laser beam by said sampling volume.

The cold plasma may be formed in air (i.e. in an atmosphere mainly comprising air).

Nevertheless, it is also possible for the cold plasma to be formed in an inert gas, e.g. in argon or helium. Under such circumstances, the elements C, H, O, and N that might be contained in the particles can advantageously be analyzed without interference from the same elements that are usually contained in air, unlike that which occurs when the method is performed in a plasma formed in air.

Thus, when the cold plasma is formed in an inert gas, the method of the invention makes it possible to detect and/or analyze carbon-containing particles. It is thus possible to analyze carbon-containing particles without interference from carbon in the air. One particular application is stoichiometric analysis of carbon nanotubes containing metallic elements.

In a particularly advantageous implementation, during steps b) and c), the particles are maintained in levitation. Advantageously, because the particles are maintained in levitation, a small number of particles suffices for performing the method.

In this implementation, the cold plasma is usually made for the purpose of analyzing particles; under such circumstances, the particles are generally deliberately injected into the plasma in order to be analyzed therein.

Compared with conventional spectrometry, the advantage of this method is that by putting particles into levitation, the laser shot does not strike matter other than the matter of the particles (ignoring the gas in which the particles are to be found, however as mentioned above, in the emission spectra, the portion that can be attributed to molecules of the gas generally remains very low). Thus, the emission spectrum does not have any interfering emissions other than a marginal amount of lines emitted by the gas present in the plasma.

The method as defined in this way thus presents a high degree of accuracy.

Furthermore, analyzing particles in levitation that are trapped in the sample volume under analysis makes it possible to analyze particles that are present in extremely small quantities, since the analysis may go down to analyzing individual particles.

This method can thus advantageously be applied to detecting and/or analyzing particles that are present only in the state of traces in the gas under consideration.

The particles may be put into levitation in particular by maintaining them between an electrode powered by a voltage that is either an RF voltage or else a direct current (DC) voltage, relative to a second electrode at a fixed potential, e.g. ground potential. Such an arrangement makes it possible to maintain a stationary cold plasma between the electrodes.

Furthermore, maintaining a low pressure, less than 10 mbar and preferably less than 1 mbar, makes it possible under certain circumstances to ensure that the particles are spread throughout the volume of the plasma. A pressure that is too high might lead to particles occupying positions at the periphery of the plasma, thereby impeding detection and/or analysis thereof.

In an implementation, during step a), the particles are injected into the plasma mainly under the effect of gravity. Gravity constitutes particularly simple means for injecting particles into a plasma.

In an implementation, in step d), the stoichiometric composition of the particles is analyzed on the basis of the emission spectra by calculating a mean emission spectrum from a plurality of emission spectra corresponding to a plurality of laser shots.

In order to calculate the mean emission spectrum, it is possible in particular to take account only of emission spectra presenting at least one or more expected emission lines and corresponding to one or more elements present in the particles being detected or analyzed.

A second object of the invention is to provide a system for analyzing particles, in particular particles of size smaller than 1 µm, and enabling the composition of particles to be analyzed quickly.

This object is achieved by the fact that the system comprises means for creating and maintaining a cold plasma at a pressure of less than 10 mbar, and preferably less than 1 mbar, a laser source suitable for firing laser shots or pulses, and an optical spectrometer device having a light collector and an optical spectrometer connected to a detector, the optical spectrometer device enabling emission spectra of the light emitted by the plasma as a result of the laser shots to be acquired in such a manner that for each acquired spectrum the acquisition period begins no later than 100 ns after firing the laser shot.

The optical spectrometer is naturally arranged in such a manner as to receive the portion of the radiation emitted by the plasma as a result of a laser shot that is collected by the light collector.

The detector or sensor connected to the optical spectrometer serves to record the spectrum, preferably resolved in time. It is desirable for time resolution to be no greater than about 2 ns in order to be able to determine accurately the beginning and the end of the acquisition period for emission spectra. The detector may be constituted in particular by an intensified charge-coupled device (CCD) camera.

The light collector may be constituted in particular mainly by a lens or a plurality of lenses. The lens(es) then has/have the function of concentrating the light emitted by the plasma and of directing it to the spectrometer, e.g. via an optical fiber. It is not necessary to use a telescope.

In an embodiment, the means for creating and maintaining a cold plasma are arranged to contain the plasma and to maintain particles in levitation therein. There is thus no contact between the particles and the enclosure or any other wall or any other body; this makes it possible to ensure that detection and/or composition analysis does indeed relate to the particles present in the plasma.

In particular, in an embodiment, the means for creating and maintaining a cold plasma comprise an enclosure having electrodes placed therein and means for applying a voltage to the electrodes in such a manner that the particles present in the plasma are kept in levitation in the plasma, and the system also has a device for injecting particles into the enclosure.

The cold plasma is then formed between the electrodes. In particular, the plasma may be generated by the electrodes under the effect of a voltage delivered by a voltage source coupled to the electrodes and controlled by a tuning box device.

The voltage may be controlled in such a manner that the particles become distributed in uniform manner in the plasma. The regularity or the uniformity of this distribution can easily be monitored visually, providing the enclosure has transparent portholes enabling the plasma between the electrodes to be seen.

The cold plasma generated between the electrodes then acts as a trap for the particles that are introduced into the plasma, i.e. it maintains them in levitation, thereby making it possible to fire the laser shots and to make the spectrometry acquisitions.

The plasma may be formed in a gas (where the term "gas" is used to mean an atmosphere essentially comprising gas, but possibly including particles in suspension) in which the particles are present even before the plasma is formed.

In another embodiment, the system includes a system for injecting the particles for analysis into the plasma: the particles are then injected into the plasma after the plasma has been formed.

In the system of the invention, the cold plasma is maintained at low pressure (e.g. a few millibars, or indeed less than 1 mbar). For this purpose, in an embodiment, the system may include an enclosure together with a vacuum pump suitable for maintaining the enclosure under a pressure of less than 10 mbar, and preferably less than 1 mbar.

In an embodiment, the means for creating and maintaining a cold plasma are adapted to create and maintain a plasma in which the concentration of particles is less than $10^8$ particles/cm$^3$, or indeed $10^6$ particles/cm$^3$, or even $10^5$ particles/cm$^3$.

The optical spectrometer device is thus adapted to acquire emission spectra in step c) that come from a plasma containing a concentration of particles that is less than $10^8$ particles/cm$^3$, or indeed $10^6$ particles/cm$^3$, or even $10^5$ particles/cm$^3$.

The invention can be well understood and its advantages appear better on reading the following detailed description of implementations given as non-limiting examples. The description refers to the accompanying drawings, in which.

Figure 1:
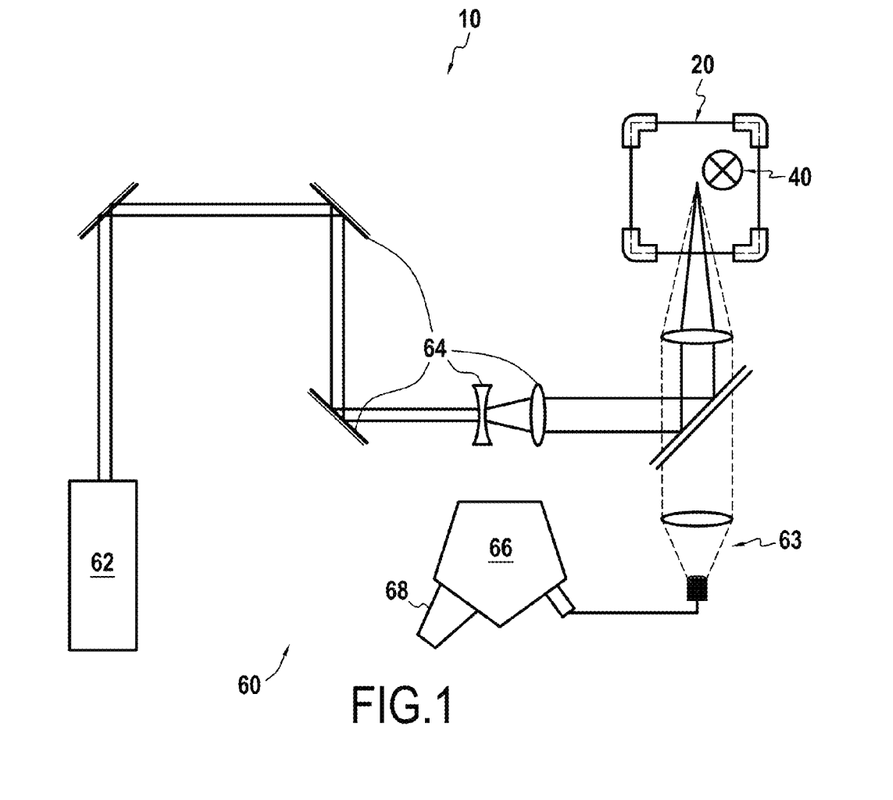
FIG. 1 is a diagrammatic plan view of a system of the invention for detecting and analyzing particles.

A system 10 of the invention for detecting and analyzing particles is shown in FIG. 1. The system 10 is made up of three main elements:

an RF plasma cell 20;
a powder injector 40; and
a spectrometer device 60.

The Plasma Cell (20)

Figure 2:
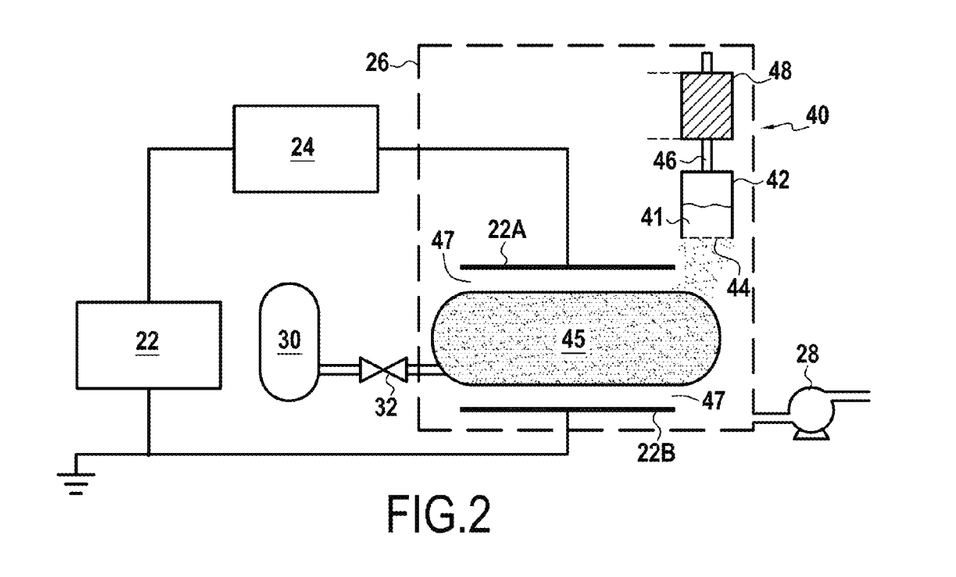
FIG. 2 is a side view of the plasma cell and of the powder injector of the FIG. 1 system.

FIG. 2 is a diagram of the plasma cell 20.

The plasma cell 20 essentially comprises a power-regulated RF generator 22, a tuning box 24, and a reactor 26.

The reactor or enclosure 26 comprises a rectangular chamber made of stainless steel having a height of 10 centimeters (cm) and a width of 10 cm, which chamber is provided with four optical portholes or windows for optical diagnostics. There must be at least two portholes facing each other in order to pass the laser beam and to analyze the plasma. These portholes should preferably be made of quartz so as to pass ultraviolet radiation (wavelengths shorter than 400 nanometers (nm)) emitted by the plasma and containing information about the chemical nature of the elements being analyzed.

Two electrodes 22 (references 22A and 22B) in the form of disks having a diameter of 6 cm and spaced apart from each other by 5 cm are arranged inside the reactor 26. The top electrode 22A is connected to the output terminal of the RF generator 22, while the bottom electrode 22B is connected to ground.

A vacuum pump 28 serves to maintain a constant pressure in the range 0.1 mbar to 1 mbar inside the reactor 26.

A cylinder of argon 30 is connected to the reactor 26 via a valve 32. It serves to replace the air contained in the reactor 26 with argon when particle detection and analysis needs to be performed in an atmosphere of argon and not air (it would also be possible to use a cylinder of nitrogen or of helium in order to enable the cold plasma to be formed in one or other of those gases).

The cell 20 enables a cold plasma to be formed as follows:

Firstly, depending on the analysis that is to be performed on the particles, the reactor 26 is placed under an atmosphere of air or of argon. The reactor 26 is taken to a pressure of 0.25 mbar by the vacuum pump 28.

Electric discharges are then applied by the electrodes 22. These discharges enable a cold plasma 45 to be created between the electrodes 22. The exciting voltage has a frequency of 13.56 megahertz (MHz), it naturally being possible to use other frequencies, mainly in the RF range.

Very quickly after the plasma 45 has been formed, space charge sheaths 47 are created. These sheaths balance the loss of electrons and of positive ions in all of the walls and electrodes that are in contact with the plasma. Consequently they confine the electrons and negatively-charged species.

When particles (in the solid state) are injected into the plasma, they become negatively charged very quickly by electrons becoming attached thereto. This is due to the mobility of electrons being large compared with the mobility of positive ions, which are much heavier.

Consequently, the particles are trapped in the volume occupied by the plasma 45 in the reactor 26 and they remain levitated therein so long as the plasma is formed.

Powder Injector (40)

The powder injector placed in the reactor 26 serves to introduce into the plasma 45 the powder 41 made up of the particles to be analyzed.

The injector 40 mainly comprises a powder container 42, that is cylindrical with a diameter of 1 cm and a height of 0.5 cm (proportions are not complied with in FIG. 2). The face of the injector for pouring particles into the plasma in the manner that is described below is formed by a grid 44 pierced by square holes having a side of 5 μm.

The container 42 is secured to a rod 46 placed in the airgap of an electromagnet 46. When the electromagnet is activated, the rod reciprocates vertically up and down. The shaking thus applied to the container 42 causes particles to pass through the grid.

In order to enable particles to be injected into the RF plasma, the container 42 is placed above the electrode 22A, not vertically above it, but rather a little outside the outer limit of the electrode (as seen from above). Consequently, the particles drop under gravity directly into the plasma 45, which captures them, since the plasma 45 occupies a volume that bulges from the side and extends horizontally around the volume defined by the electrodes, as shown in FIG. 2.

The Laser-Induced Spectrometer Device (60)

The device 60 comprises a laser source 62, a light collector 63, a set 64 of mirrors and of lenses, including in particular a dichroic mirror, for conveying the laser beam and the radiation emitted by the laser-induced microplasma on the particles, and an optical spectrometer 66.

The laser source 62 serves to fire laser shots having a wavelength of 1064 nm, with each shot having energy of 340 millijoules (mJ) and a pulse duration of 5 ns. The optical path used for the setup is shown in FIG. 1.

The light collector 63 serves to receive the light emitted by the plasma as a result of a laser. This light is collected and conveyed via an optical fiber to the spectrometer 66.

The light collector is adjusted to collect as well as possible the light emitted by the laser-induced microplasma on the particles, and not the radiation emitted by the cold plasma 45.

The spectrometer 66 is a spectrometer of Czerny-Turner type. It is used with a spectral window of 30 nm.

The spectrometer 66 is connected to a detector. In the system 10, the detector is an intensified CCD camera 68 capable of recording a spectrum with a minimum time resolution of about 2 ns (it is optionally possible to make use of other detectors that are simpler).

The experimental spectra described below plot the intensity of the signal received by the spectrometer as a function of the wavelength $\lambda$ of the radiation.

These spectra were recorded using the following time parameters for the detector: the acquisition delay $t_d$ represents the time that elapses between firing the laser shots and beginning to record the signal with the camera; and the integration time $\Delta t$ represents the duration of the exposure of the CCD matrix 68 to the light signal from the plasma.

Performing the Analysis and Detection Method

Creating the Plasma and Acquiring Emission Spectra

The method of the invention is described below in two implementations, corresponding to two batches of nanoparticles synthesized by laser pyrolysis:

a powder of $Al_2O_3$ nanoparticles of spherical shape, having a diameter of 350 nm; and
 a powder of SiC nanoparticles of non-spherical shape with median and maximum particle diameters of 800 nm and of 1200 nm, respectively.

The system 10 is used in two stages.

Firstly, a plasma 45 is created between the electrodes 22 of the reactor 26. (The method of the invention may naturally be applied to other cold plasmas, regardless of their origin or the method used for forming them.)

Thereafter, the spectrometer device 60 is used to detect the elements (specifically Al, O, Si, and C) contained in the particles being analyzed. To do that, the following operations are performed:

firing a laser shot into the plasma 45 using the laser source 62;
 the radiation reflected by the plasma is collected by the collector 63 and directed to the spectrometer 66;
 for each laser shot, the spectrometer 66 produces a spectrum of lines corresponding to the various elements that have been subjected to the laser shot; and
 the spectrum (or spectra) produced by the spectrometer is/are analyzed in order to detect the presence of particles, and/or in order to analyze the stoichiometric composition of the particles, and/or in order to evaluate the concentration of particles in the plasma.

When acquiring various emission spectra, the acquisition window begins after an acquisition delay $t_D$ of less than 100 ns after the laser shot, e.g. of 30 ns.

The lines corresponding to the elements making up the particles under analysis are shown in Table 1. (No line is marked for oxygen, since the measurements were performed in air, but at low pressure. Consequently detecting oxygen would have provided no information about the nature of the particles, and therefore was not performed.)

TABLE 1

| Element | $\lambda$ (nm) | Aki ($10^7 s^{-1}$) | Ei (eV) | Ek (eV) |
|---|---|---|---|---|
| Al I | 394.40058 | 4.93 | 0.0 | 3.1427210 |
|  | 396.15200 | 9.8 | 0.0138938 | 3.1427210 |
| C I | 247.856 | 2.8 | 2.684011 | 7.684766 |
| Si I | 288.1579 | 21.7 | 0.7809578 | 5.0823456 |

Table 1 gives the wavelengths $\lambda$, the transition probability coefficients Aki, and the lower and higher energy levels Ei and Ek of neutral lines of Al, C, and Si as detected by analyzing particles $SiC_x$ and of $Al_2O_3$.

Making Use of Emission Spectra

The laser-induced spectrometer device 60 serves to record a signal (or a spectrum) for each laser shot.

Such spectra are shown in FIGS. 3A to 7B.

Figure 3A:
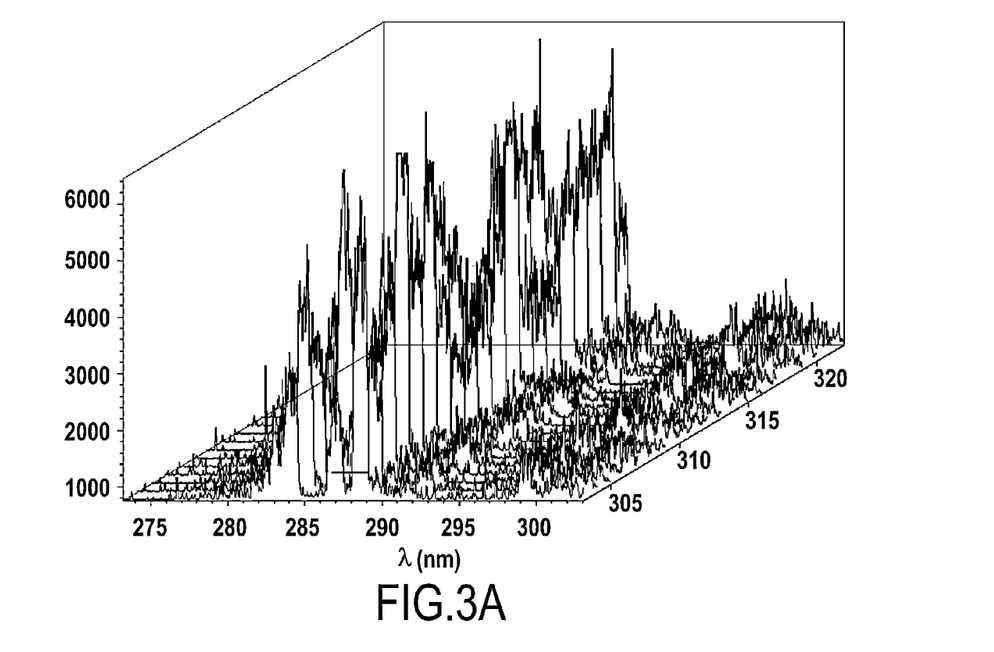
FIGS. 3A and 3B show pluralities of emission spectra obtained by the FIG. 1 system, respectively for particles of Al$_2$O$_3$ (FIG. 3A) and of SiC (FIG. 3B)
Figure 3B:
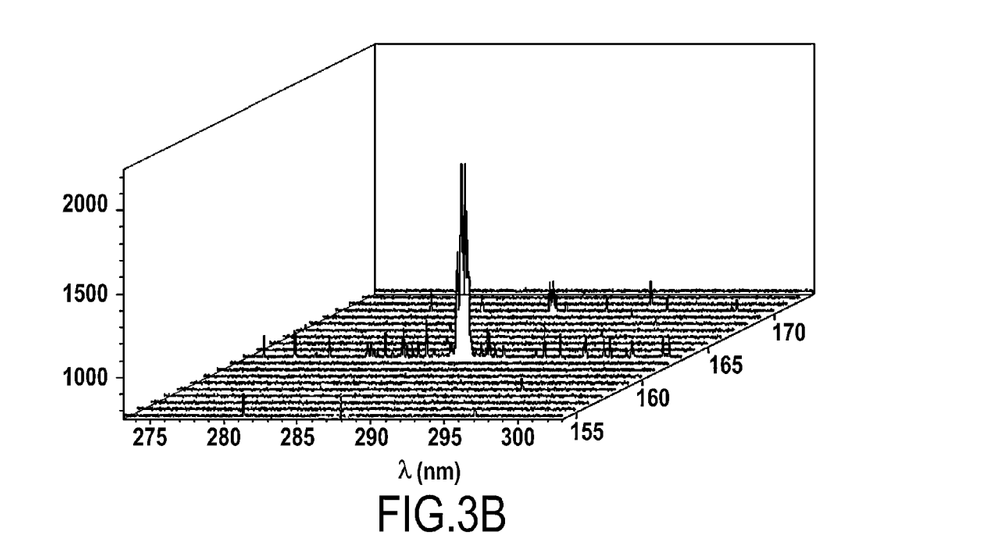

A first observation is that when using $Al_2O_3$ powders, each laser shot causes aluminum lines to appear (FIG. 3A). Conversely, when using SiC powders, only a small proportion of the laser shots cause lines characteristic of silicon to appear (FIG. 3B). It is concluded that an SiC particle is hit by only a small proportion of laser shots (i.e. a particle lies in the sampling volume at the time the laser shot was fired for only a small proportion of shots). More precisely, among the laser shot spectra shown in FIG. 3B, only one of the shots hits a particle of SiC and consequently caused silicon lines to be emitted.

The system 10 is thus sufficiently sensitive to be capable of detecting the presence of a single particle! More generally, the rate at which silicon lines are detected is naturally a function of the concentration of particles in the plasma 45.

Furthermore, in FIG. 3B, it can be seen that when no particle is hit by the laser shot, the radiation picked up by the spectrometer is insignificant, which results from the fact that no microplasma is created within the enclosure by the laser shot.

Figure 4A:
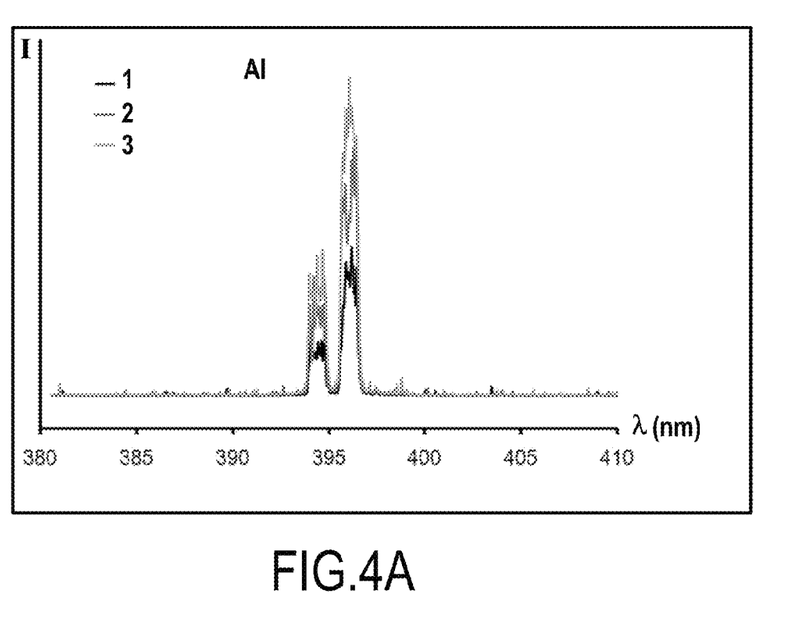
FIGS. 4A and 4B show individual emission spectra obtained by the FIG. 1 system, respectively for particles of Al$_2$O$_3$ (FIG. 4A) and of SiC (FIG. 4B)
Figure 4B:
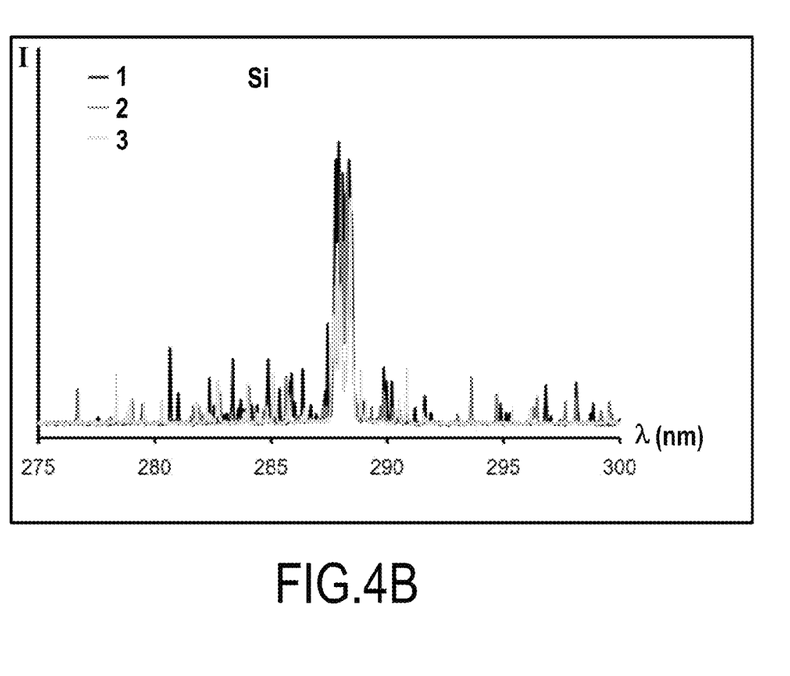

A difficulty that can arise in certain circumstances for analyzing particle composition on the basis of spectra provided by the spectrometer lies in a certain amount of variability in the spectra that are obtained when using a single laser shot. This variability is shown in FIGS. 4A and 4B. Each of these figures shows the spectra obtained during three different laser shots. FIG. 4A shows mainly aluminum lines (the particles were of $Al_2O_3$), and FIG. 4B shows mainly silicon lines (the particles were of SiC).

In order to remedy this problem, the analysis of the spectra obtained is performed in the system 10 on the basis of a mean spectrum. This is calculated by taking the average of the spectra obtained for a plurality of laser shots.

Figure 5A:
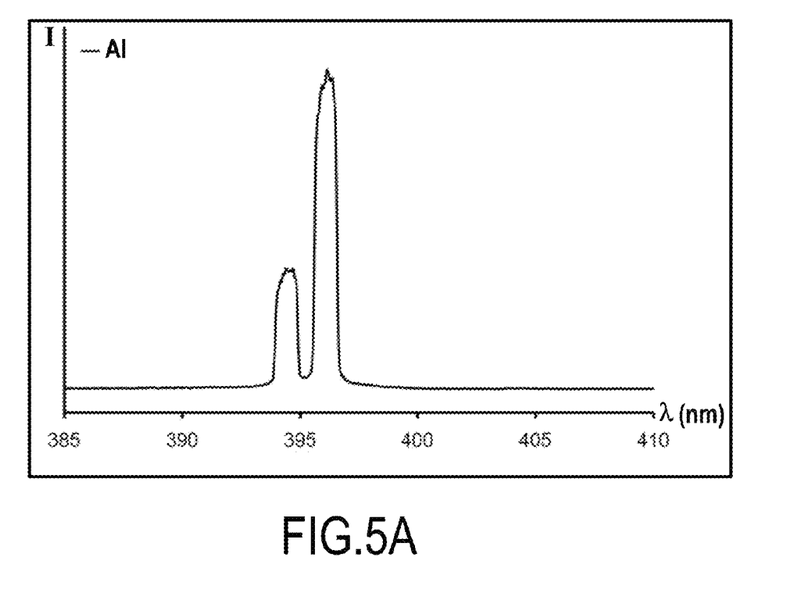
FIGS. 5A and 5B show averaged emission spectra obtained by the FIG. 1 system, respectively for particles of Al$_2$O$_3$ (FIG. 5A) and of SiC (FIG. 5B)
Figure 5B:
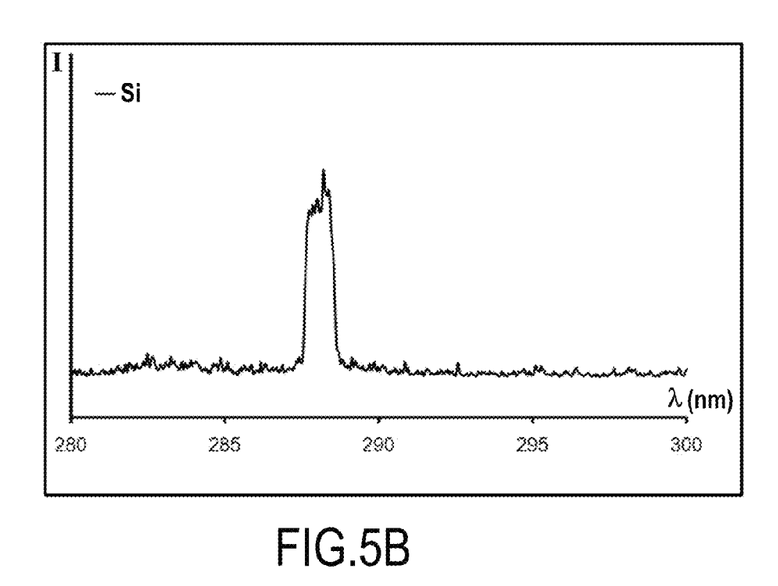

FIGS. 5A and 5B show an example of spectra obtained by averaging a plurality of laser shots (specifically 1400 shots) for aluminum lines (FIG. 5A) and for silicon lines (FIG. 5B).

In order to reduce background noise in the mean spectrum, when determining the mean spectrum, it is preferable to use only those spectra that include the looked-for lines (of aluminum or of silicon, respectively).

Determining the Stoichiometry of the Particles

On the basis of the spectra provided by the optical spectrometer (possibly averaged as described above), it is possible to determine the stoichiometry of the particles present in the plasma.

The stoichiometry is calculated by determining the ratios between the intensities of the emission lines of the various identified components. Various methods of calculation are possible; for greater detail, reference may be made for example to one of the following French patent applications FR 2 937 419 and FR 2 938 066.

Estimating Concentrations

The system 10 also makes it possible to calculate or to estimate the concentration of particles in the plasma.

The volume sampled by the laser beam can be approximated by the focal volume, assuming that it occupies a perfect Gaussian beam. The sampling volume is estimated using the following equation:

$$V = 19.2 (f/D)^4 \lambda^3 \quad \text{(equation 1)}$$

in which:
  V is the sampling volume of the laser beam;
  f is the focal length of the lens;
  D is the diameter of the laser beam; and
  λ is the wavelength of the laser beam.

The estimated focal volume is $10^{-8}$ cm$^3$.

On the basis of the sampling volume and by calculating the ratio between the number of shots in which silicon lines are observed and the total number of shots, it is possible to determine the concentration of SiC particles in the plasma 45 under study.

With particles of $Al_2O_3$, the sampling rate is 100%. This means that there is always at least one particle in the focal volume. Consequently, it is possible to deduce a minimum concentration for the particles: this is $10^8$ particles per cm$^3$ or greater for nanoparticles of $Al_2O_3$.

When particles are present in very small quantity, the concentration of SiC particles can on the contrary be estimated as contrasted to being underestimated (as with particles of $Al_2O_3$).

The analysis of SiC particles shown in FIG. 3B can be used by way of example.

In the plasma under consideration, very few laser shots give rise to the appearance of a spectrum indicating that a particle was hit by the laser shot. The particles are very dilute, and on most occasions there are no particles or only one particle in the sampling volume.

The system 10 thus makes it possible to distinguish between circumstances in which the laser shot hits a particle of SiC and circumstances in which it does not hit any. It is therefore possible to calculate the fraction or percentage of laser shots that hit a particle of SiC. This percentage can be considered as being a probability of a particle being present in the sampling volume of the laser shot.

On the basis of this information, an estimate is thus obtained of the concentration of particles of SiC in the plasma by dividing the percentage by the previously calculated sampling volume.

Figure 6:
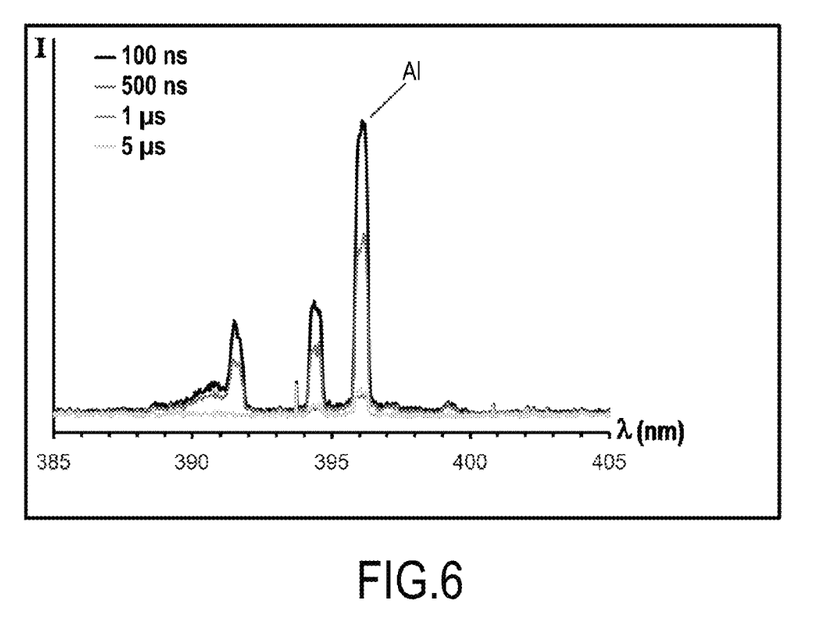
FIG. 6 shows emission spectra obtained by the FIG. 1 system for particles of Al$_2$O$_3$ for different values for the delay between firing the laser and the beginning of recording with the optical spectrometer.

Variation in the Intensity of the Signal as Function of the Acquisition Delay $t_D$ Between Firing the Laser Shot and the Beginning of Recording the Signal The intensity of the spectroscopic signal has been studied as a function of the delay $t_d$ between firing the laser shot and the beginning of recording the signal. The corresponding spectra are shown in FIG. 6. These spectra show that the lifetime of the signal does not exceed a few microseconds. Furthermore, the intensity of the background noise does not vary as a function of the delay so the signal-to-noise ratio is optimized for shorter delays, i.e. delays $t_D$ that are less than about 100 ns.

This number emphasizes the importance of a short acquisition delay $t_D$ between firing the laser shot and beginning recording by means of the spectrometer.

The invention claimed is:

1. An analysis method for analyzing particles, in particular particles of diameter less than 1 μm, the method comprising the following steps:
   a) providing a cold plasma at a pressure less than 10 mbar;
   b) firing laser shots into the cold plasma;
   c) using an optical spectrometer device to acquire emission spectra of the light emitted by the plasma as a result of the laser shots, in such a manner that for each acquired spectrum, an acquisition period begins no later than 100 ns after firing the laser shot; and
   d) analyzing the particles present in the plasma on the basis of said emission spectra.

2. An analysis method according to claim 1, wherein during steps b) and c), the particles are kept levitated in the plasma.

3. An analysis method according to claim 1, wherein the particles are kept in levitation between an electrode powered by a voltage that is either RF or else DC, relative to a second electrode at a fixed potential, e.g. ground potential.

4. An analysis method according to claim 1, wherein the concentration of particles in the cold plasma is less than $10^8$ particles/cm$^3$, or indeed $10^6$ particles/cm$^3$, or even $10^5$ particles/cm$^3$.

5. An analysis method according to claim 1, wherein, during step a), the particles are injected into the plasma mainly under the effect of gravity.

6. An analysis method according to claim 1, wherein, in step d), the stoichiometric composition of the particles is analyzed on the basis of the emission spectra by calculating a mean emission spectrum from a plurality of emission spectra corresponding to a plurality of laser shots.

7. An analysis method according to claim 1, wherein, in order to acquire the emission spectra in step c), the optical spectrometer device has at least one lens used for concentrating the light emitted by the plasma.

8. An analysis system for analyzing particles, in particular particles of dimensions less than 1 μm, the system comprising:
   a plasma generator for creating and maintaining a cold plasma at a pressure of less than 10 mbar, and preferably less than 1 mbar;
   a laser source suitable for firing laser shots into the plasma; and
   an optical spectrometer device having a light collector and an optical spectrometer connected to a detector,
      the optical spectrometer device enabling emission spectra of the light emitted by the plasma as a result of the laser shots to be acquired in such a manner that for each acquired spectrum an acquisition period begins no later than 100 ns after firing the laser shot.

9. An analysis system according to claim 8, wherein said plasma generator comprises an enclosure having electrodes placed therein and a power supply for applying a voltage to the electrodes in such a manner that the particles present in the plasma are kept in levitation in the plasma, the analysis system also having a device for injecting particles into the enclosure.

10. An analysis system according to claim 8, in which the plasma generator is adapted to create and maintain a plasma presenting a concentration of particles that is less than $10^8$ particles/cm³, or indeed 10⁶ particles/cm³, or even 10⁵ particles/cm³; and in step c), the acquired emission spectra come from said plasma containing a concentration of particles that is less than 10⁸ particles/cm³, or indeed 10⁶ particles/cm³, or even 10⁵ particles/cm³.

11. An analysis system according to claim 8, in which the light collector includes at least one lens suitable for concentrating the light emitted by the plasma.

12. An analysis method for analyzing particles according to claim 1, wherein the diameter of the particles is less than 1 μm.

13. An analysis method for analyzing particles according to claim 1, wherein at step a), the cold plasma is provided at a pressure less than 1 mBar.

* * * * *